(12) United States Patent
Do et al.

(10) Patent No.: US 8,066,956 B2
(45) Date of Patent: Nov. 29, 2011

(54) DELIVERY OF AN ODOR CONTROL AGENT THROUGH THE USE OF A PRESATURATED WIPE

(75) Inventors: Bao Trong Do, Decatur, GA (US); John Gavin MacDonald, Decatur, GA (US); Stephanie Michelle Martin, Woodstock, GA (US); Duane G. Uitenbroek, Little Chute, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 737 days.

(21) Appl. No.: 11/640,115

(22) Filed: Dec. 15, 2006

(65) Prior Publication Data

US 2008/0145267 A1 Jun. 19, 2008

(51) Int. Cl.
A61L 2/00 (2006.01)
A61L 9/00 (2006.01)
C11D 17/00 (2006.01)

(52) U.S. Cl. ............... 422/292; 422/5; 510/438
(58) Field of Classification Search ............... 422/5, 292; 510/438
See application file for complete search history.

(56) References Cited

U.S. PATENT DOCUMENTS

| | | |
|---|---|---|
| 3,494,821 A | 2/1970 | Evans |
| 3,855,046 A | 12/1974 | Hansen et al. |
| 4,100,324 A | 7/1978 | Anderson et al. |
| 4,144,370 A | 3/1979 | Boulton |
| 4,659,609 A | 4/1987 | Lamers et al. |
| 4,795,668 A | 1/1989 | Krueger et al. |
| 4,833,003 A | 5/1989 | Win et al. |
| 5,057,368 A | 10/1991 | Largman et al. |
| 5,069,970 A | 12/1991 | Largman et al. |
| 5,108,820 A | 4/1992 | Kaneko et al. |
| 5,162,074 A | 11/1992 | Hills |
| 5,277,976 A | 1/1994 | Hogle et al. |
| 5,284,703 A | 2/1994 | Everhart et al. |
| 5,336,552 A | 8/1994 | Strack et al. |
| 5,350,624 A | 9/1994 | Georger et al. |
| 5,382,400 A | 1/1995 | Pike et al. |
| 5,407,600 A | 4/1995 | Ando et al. |
| 5,466,410 A | 11/1995 | Hills |

(Continued)

FOREIGN PATENT DOCUMENTS

EP 1405632 A1 4/2004

(Continued)

OTHER PUBLICATIONS

PCT International Search Report and Written Opinion for Application No. PCT/IB2007/054700, completed Apr. 22, 2008, mailed May 2, 2008.

*Primary Examiner* — Kevin Joyner
(74) *Attorney, Agent, or Firm* — Dority & Manning, P.A.

(57) ABSTRACT

A wiping product is disclosed containing an odor control agent. In one embodiment, the wipe may comprise a pre-moistened wipe containing a wiping solution. The wiping solution can contain the odor control agent. The odor control agent may comprise inorganic oxide particles, quinone compounds, or activated carbon particles. The odor control agent can be present in the wipe and can be configured to transfer to an opposing surface. In one embodiment, the pre-moistened wipe can be used during diaper changing to reduce malodors given off by the diaper after being discarded.

19 Claims, 2 Drawing Sheets

U.S. PATENT DOCUMENTS

| | | | |
|---|---|---|---|
| 5,480,636 A | 1/1996 | Maruo et al. | |
| 5,486,356 A | 1/1996 | Yim | |
| 5,620,779 A | 4/1997 | Levy et al. | |
| 5,861,147 A | 1/1999 | Dodd et al. | |
| 5,882,638 A | 3/1999 | Dodd et al. | |
| 5,935,883 A | 8/1999 | Pike | |
| 5,948,398 A | 9/1999 | Hanamoto et al. | |
| 5,962,112 A | 10/1999 | Haynes et al. | |
| 5,989,400 A | 11/1999 | Islam | |
| 6,093,665 A | 7/2000 | Sayovitz et al. | |
| 6,103,061 A | 8/2000 | Anderson et al. | |
| 6,197,404 B1 | 3/2001 | Varona | |
| 6,200,639 B1 | 3/2001 | Duecoffre et al. | |
| 6,294,186 B1 | 9/2001 | Beerse et al. | |
| 6,315,864 B2 | 11/2001 | Anderson et al. | |
| 6,322,665 B1 | 11/2001 | Sun et al. | |
| 6,429,261 B1 | 8/2002 | Lang et al. | |
| 6,444,214 B1 | 9/2002 | Cole et al. | |
| 6,488,943 B1 * | 12/2002 | Beerse et al. | 424/401 |
| 6,548,592 B1 | 4/2003 | Lang et al. | |
| 6,579,570 B1 | 6/2003 | Lang et al. | |
| 6,586,529 B2 | 7/2003 | Mumick et al. | |
| 6,599,848 B1 | 7/2003 | Chen et al. | |
| 6,602,955 B2 | 8/2003 | Soerens et al. | |
| 6,610,174 B2 | 8/2003 | Sun et al. | |
| 6,653,406 B1 | 11/2003 | Soerens et al. | |
| 6,683,143 B1 | 1/2004 | Mumick et al. | |
| 6,713,414 B1 | 3/2004 | Pomplun et al. | |
| 6,716,498 B2 | 4/2004 | Curro et al. | |
| 6,716,805 B1 | 4/2004 | Sherry et al. | |
| 6,814,974 B2 | 11/2004 | Cole et al. | |
| 6,815,502 B1 | 11/2004 | Lang et al. | |
| 6,824,650 B2 | 11/2004 | Lindsay et al. | |
| 6,828,014 B2 | 12/2004 | Branham et al. | |
| 6,835,678 B2 | 12/2004 | Jackson et al. | |
| 6,897,168 B2 | 5/2005 | Branham et al. | |
| 6,908,966 B2 | 6/2005 | Chang et al. | |
| 6,911,114 B2 | 6/2005 | Lindsay et al. | |
| 6,916,402 B2 | 7/2005 | Shannon et al. | |
| 6,926,931 B2 | 8/2005 | Qashou et al. | |
| 6,936,580 B2 | 8/2005 | Sherry et al. | |
| 6,960,371 B2 | 11/2005 | Bunyard et al. | |
| 6,994,865 B2 | 2/2006 | Branham et al. | |
| 2003/0027470 A1 | 2/2003 | Chang et al. | |
| 2003/0032352 A1 | 2/2003 | Chang et al. | |
| 2003/0135939 A1 | 7/2003 | Sun et al. | |
| 2003/0203009 A1 | 10/2003 | MacDonald | |
| 2003/0220042 A1 | 11/2003 | Lostocco et al. | |
| 2004/0055704 A1 | 3/2004 | Bunyard et al. | |
| 2004/0058600 A1 | 3/2004 | Bunyard et al. | |
| 2004/0058606 A1 | 3/2004 | Branham et al. | |
| 2004/0063888 A1 | 4/2004 | Bunyard et al. | |
| 2004/0120904 A1 | 6/2004 | Lye et al. | |
| 2004/0121681 A1 | 6/2004 | Lindsay et al. | |
| 2005/0026802 A1 | 2/2005 | Kilkenny et al. | |
| 2005/0084412 A1 | 4/2005 | MacDonald et al. | |
| 2005/0084438 A1 | 4/2005 | Do et al. | |
| 2005/0084464 A1 | 4/2005 | McGrath et al. | |
| 2005/0084474 A1 | 4/2005 | Wu et al. | |
| 2005/0085144 A1 | 4/2005 | MacDonald et al. | |
| 2005/0113771 A1 | 5/2005 | MacDonald et al. | |
| 2005/0131363 A1 | 6/2005 | MacDonald et al. | |
| 2005/0136238 A1 | 6/2005 | Lindsay et al. | |
| 2006/0003649 A1 | 1/2006 | Runge et al. | |
| 2006/0003654 A1 | 1/2006 | Lostocco et al. | |
| 2006/0008442 A1 | 1/2006 | MacDonald et al. | |
| 2006/0018966 A1 * | 1/2006 | Lin et al. | 424/484 |
| 2006/0137568 A1 | 6/2006 | MacDonald et al. | |
| 2006/0140902 A1 | 6/2006 | MacDonald et al. | |
| 2006/0142828 A1 | 6/2006 | Schorr et al. | |
| 2006/0165622 A1 * | 7/2006 | Hiramoto et al. | 424/65 |

FOREIGN PATENT DOCUMENTS

| | | |
|---|---|---|
| WO | WO 91 12030 | 8/1991 |
| WO | WO 96 24318 | 8/1996 |
| WO | WO 98 26808 | 6/1998 |
| WO | WO 2005 039655 A1 | 5/2005 |
| WO | WO 2005 039661 A1 | 5/2005 |
| WO | WO 2006038931 A2 | 4/2006 |

* cited by examiner

DELIVERY OF AN ODOR CONTROL AGENT THROUGH THE USE OF A PRESATURATED WIPE

BACKGROUND

Saturated or pre-moistened wiping products have been used in a variety of wiping and polishing applications. Perhaps the most common form is a stack of individual, folded sheets packaged in a plastic container for use as baby wipes. Wet wipes are also available containing antimicrobial compositions for cleaning desired surfaces. Wet wipes are typically used only once and then discarded.

Wet wipes designed to clean or disinfect adjacent surfaces are typically made from liquid absorbent, textile substrates. The substrates, for instance, may contain synthetic fibers alone or in conjunction with natural fibers. For instance, some wet wipe materials are made from airlaid webs that have been treated with a water insoluble adhesive or spunlace webs containing water insoluble synthetic fibers. Wet wipe materials may also contain meltspun webs, such as meltblown webs, spunbond webs, coform webs, and laminates thereof. Recently, water dispersible wet wipes have also been produced that degrade when submerged in a wet environment.

Although pre-moistened wipes function well to clean spills and to wipe away urine and fecal matter during a diaper changing, a need currently exists for a pre-moistened wipe that is not only configured to clean an adjacent surface but also to capture and/or reduce malodors generated from the area being cleaned. For instance, a need currently exists for a baby wipe that not only is well suited to wiping away urine and/or fecal matter but also that can be configured to reduce malodors coming from the child or from the diaper itself. Pre-moistened wipes with odor control properties are also needed for cleaning hard surfaces in addition to other personal care applications.

SUMMARY

In general, the present disclosure is directed to various methods for controlling malodors. More particularly, the present disclosure is directed to a pre-moistened wipe and to methods for using the wipe in order to reduce and control malodors in addition to cleaning up spills and messes on adjacent surfaces. In one particular embodiment, for instance, the pre-moistened wipe can be used during diaper changing for not only wiping away urine and fecal matter from a baby but for also later reducing malodors being emitted by the diaper after it has been discarded.

In one embodiment, for instance, the pre-moistened wipe comprises a sheet-like substrate containing a wiping solution. The sheet-like substrate can comprise any suitable liquid absorbent material. For instance, the substrate may comprise a nonwoven web. In various embodiments, for instance, the sheet-like substrate comprises a coform web, a wetlaid web, an airlaid web, or a hydroentangled web. The web can contain synthetic fibers, pulp fibers, or mixtures thereof.

The wiping solution in accordance with the present disclosure comprises an odor control agent. The odor control agent comprises inorganic oxide particles modified with a transition metal, a quinone compound, or activated carbon particles. The wiping solution can also contain at least one surfactant. The at least one surfactant may comprise a nonionic surfactant or an anionic surfactant. In one particular embodiment, for instance, the wiping solution may contain a mixture of surfactants, such as at least one nonionic surfactant and at least one anionic surfactant. In general, the wiping solution is substantially free of any surfactants that may interfere with the ability of the odor control agents to control odors. For instance, in one embodiment, the wiping solution may be substantially free of cationic surfactants.

The wiping solution may contain further ingredients, such as a carrier. The carrier may comprise water or an alcohol, such as a glycol. The odor control agent may be present in the substrate in an amount of at least about 80 milligrams, such as from about 100 milligrams to about 500 milligrams. The amount of odor control agent present in the substrate may also be based upon the dry weight of the substrate. For instance, in one embodiment, the odor control agent may be present in the substrate in an amount from about 2% to about 30% by weight based on the dry weight of the substrate, such as from about 10% to about 25% by weight.

When the odor control agent comprises the inorganic oxide particles modified with the transition metal, the inorganic oxide particles may comprise, for instance, silica particles, alumina particles, or mixtures thereof. The transition metal may comprise, for instance, copper, iron, manganese, cobalt or mixtures thereof. In one embodiment, the transition metal to inorganic oxide particle ratio can be from about 25:1 to about 75:1. In still another embodiment, the inorganic oxide particles modified with the transition metal may have a surface area of less than about 200 $m^2/g$, such as less than about 100 $m^2/g$.

When the odor control agent comprises a quinone compound, on the other hand, the quinone compound can comprise a dye. Of particular advantage, the odor control agent can be suspended within the wiping solution. Thus, the odor control agent can be added to the wiping solution prior to saturating the substrate with the solution. Once contained in the substrate, the odor control agent can be configured to transfer to an adjacent surface when contacted with the substrate. In this manner, the odor control agent can not only reduce malodors on the pre-moistened wipe after the wipe is used, but can also reduce malodors on adjacent surfaces and objects.

The ingredients contained in the wiping solution combined with the odor control agent can be carefully selected and controlled so as to not interfere with the ability of the odor control agent to reduce malodors. For instance, possible surfactants that may be contained in the wiping solution include polyoxyethylene sorbitan monolaurate, a nonionic glycerin, lauric acid, castor oil, myristic acid, oleic acid, stearyl alcohol, cetyl alcohol, potassium laureth phosphate, capric acid, stearic acid, erucic acid, or mixtures thereof.

In general, most nonionic surfactants may be combined with the odor control agent without adversely affecting the resulting solution. In one embodiment, for instance, the wiping solution can contain only nonionic surfactants. Alternatively, some anionic surfactants may also be combined with the odor control agent. The anionic surfactant may be present in combination with one or more nonionic surfactants or, alternatively, the wiping solution may only contain anionic surfactants.

In addition to surfactants, various other ingredients may be contained in the wiping solution as long as the ingredients do not adversely interfere with the odor control agent. For instance, many fragrances may be incompatible with the odor control agents. Thus, the wiping solution may be substantially fragrance free or may contain carefully selected fragrances. For instance, fragrances that may be compatible with the odor control agents include fragrances having a non-hetero atom. Such fragrances can include, for instance, hydrocarbons, such as terpenes.

Other ingredients that may be present in the wiping solution include sequestrants, skin agents, and antioxidants.

In general, the wiping solution is present in the substrate in an amount sufficient to saturate the substrate. For instance, in one embodiment, the wiping solution may be contained in the substrate in an amount from about 150% to about 600% based on the dry weight of the substrate.

In one embodiment, the present disclosure is particularly directed to a method of reducing malodors emitted by a diaper insulted with urine and/or fecal matter. The method includes the steps of removing an absorbent article from a wearer after the absorbent article has been insulted with urine or fecal matter. Any remaining fecal matter or urine is wiped off the wearer with a pre-moistened wipe made in accordance with the present disclosure. The pre-moistened wipe, for instance, may include a sheet-like substrate containing a wiping solution. The wiping solution may contain an odor control agent as described above.

After wiping the wearer of the absorbent article, in accordance with the present disclosure, the absorbent article is wrapped around the pre-moistened wipe and disposed of. Thus, the pre-moistened wipe is in direct contact with the urine and/or fecal matter contained within the absorbent article. The pre-moistened wipe ultimately reduces malodors given off by the absorbent article.

In another embodiment, the present disclosure is directed to a method of applying an odor control agent to an adjacent surface. In this embodiment, the method includes the steps of wiping an adjacent surface with a pre-moistened wipe as described above. In particular, the pre-moistened wipe comprises a sheet-like substrate containing a wiping solution. The wiping solution contains at least one odor control agent in combination with various other ingredients. During the wiping step, at least a portion of the odor control agent contained in the pre-moistened wipe transfers to the adjacent surface.

For example, in one embodiment, the pre-moistened wipe may be configured to transfer from about 0.5 gsm to about 5 gsm of the odor control agent to an adjacent surface when contacted with the adjacent surface. For example, when the pre-moistened wipe is contacted with an adjacent surface, from about 10% to about 50% by weight of the wiping solution may be transferred to the surface.

Other features and aspects of the present disclosure are discussed in greater detail below.

DETAILED DESCRIPTION

It is to be understood by one of ordinary skill in the art that the present discussion is a description of exemplary embodiments only, and is not intended as limiting the broader aspects of the present invention.

Spills and messes are a normal occurrence for consumers. Often the spills and messes will carry with them an inherent undesirable odor. While various wipers are available for cleaning up spills and messes effectively, the disposal of the used wiper does not guarantee that the remnants of the spills and messes will be eliminated. In particular, odors can still be generated from the spills and can still be released from the used wipers. Eventually such wipers can emit noticeable malodors when combined with other garbage.

The present disclosure is generally directed to a wipe that has odor control functionality in addition to cleaning functionality. The wipe, for instance, while maintaining its function to clean spills and messes by absorption, has the ability to capture and/or reduce malodors generated from the area being cleaned. The captured malodors are not re-emitted into the environment and thus cannot be detected during and after disposal. In one particular embodiment, the wipe is pre-moistened with a cleaning solution containing one or more odor control agents. The wipe can be used in various and numerous applications. For instance, the wipe can be used to clean hard surfaces found in kitchens, bathrooms, food industries, hospitals, and the like. The wipe can also be used in personal care applications. For instance, the wipe can be used as a baby wipe or as a hand and body cleaning wipe.

In one particular application, for instance, the wipe of the present disclosure may comprise a pre-moistened baby wipe. The baby wipe, for example, may be used during a diaper change. Due to the presence of one or more odor control agents, the baby wipe, in addition to removing and cleaning urine and/or fecal matter from a baby, can reduce malodors. More particularly, the baby wipe of the present disclosure can reduce odors while the diaper change occurs which may provide discretion to the caregiver and child and maintain a clean smelling environment. Of particular advantage, the baby wipe can be combined with the soiled diaper and can also reduce or prevent malodors after the soiled diaper is disposed. For instance, the baby wipe can control odors during short-term disposal when the diaper is thrown in home garbage and can control odors during long-term disposal when the diaper sits in a garbage can and is hauled away.

In general, the wiper of the present disclosure comprises a liquid absorbent substrate containing at least one odor control agent. In one embodiment, the substrate can be pre-moistened with a wiping solution containing the odor control agent.

The liquid absorbent substrate can be formed from a variety of materials. For example, the substrate can include a nonwoven fabric, woven fabric, knit fabric, wet-strength paper, or combinations thereof. Materials and processes suitable for forming such substrate are well known to those skilled in the art.

For instance, some examples of nonwoven fabrics that may be used in the present disclosure include, but are not limited to, spunbonded webs (apertured or non-apertured), melt-blown webs, bonded carded webs, air-laid webs, coform webs, hydraulically entangled webs, and the like. In addition, nonwoven fabrics can contain synthetic fibers (e.g., polyethylenes, polypropylenes, polyvinyl chlorides, polyvinylidene chlorides, polystyrenes, polyesters, polyamides, polyimides, etc.); cellulosic fibers (softwood pulp, hardwood pulp, thermomechanical pulp, etc.); or combinations thereof.

If desired, the nonwoven fabric may also be bonded using techniques well known in the art to improve the durability, strength, hand, aesthetics, texture, and/or other properties of the fabric. For instance, the nonwoven fabric can be thermally (e.g., pattern bonded), ultrasonically, adhesively and/or mechanically (e.g., through-air dried) bonded. For instance, various pattern bonding techniques are described in U.S. Pat. No. 3,855,046 to Hansen; U.S. Pat. No. 5,620,779 to Levy, et al.; U.S. Pat. No. 5,962,112 to Haynes, et al.; U.S. Pat. No. 6,093,665 to Sayovitz, et al.; U.S. Design Pat. No. 428,267 to Romano, et al.; and U.S. Design Pat. No. 390,708 to Brown, which are incorporated herein in their entirety by reference thereto for all purposes.

The nonwoven fabric can be bonded by continuous seams or patterns. As additional examples, the nonwoven fabric can be bonded along the periphery of the sheet or simply across the width or cross-direction (CD) of the web adjacent the edges. Other bond techniques, such as a combination of thermal bonding and latex impregnation, may also be used. Alternatively and/or additionally, a resin, latex or adhesive may be applied to the nonwoven fabric by, for example, spraying or printing, and dried to provide the desired bonding. Still other suitable bonding techniques may be described in U.S. Pat. No. 5,284,703 to Everhart, et al., U.S. Pat. No. 6,103,061 to Anderson, et al., and U.S. Pat. No. 6,197,404 to Varona, which are incorporated herein in its entirety by reference thereto for all purposes.

In one embodiment of the present disclosure, the substrate is formed from a hydroentangled nonwoven fabric. Hydroentangling processes and hydroentangled composite webs containing various combinations of different fibers are known in the art. A typical hydroentangling process utilizes high pressure jet streams of water to entangle fibers and/or filaments to form a highly entangled consolidated fibrous structure, e.g., a nonwoven fabric. Hydroentangled nonwoven fabrics of staple length fibers and continuous filaments are disclosed, for example, in U.S. Pat. No. 3,494,821 to Evans and U.S. Pat. No. 4,144,370 to Bouolton, which are incorporated herein in their entirety by reference thereto for all purposes. Hydroentangled composite nonwoven fabrics of a continuous filament nonwoven web and a pulp layer are disclosed, for example, in U.S. Pat. No. 5,284,703 to Everhart, et al. and U.S. Pat. No. 6,315,864 to Anderson, et al., which are incorporated herein in their entirety by reference thereto for all purposes.

In another embodiment, the substrate is formed from a spunbonded web containing monocomponent and/or multicomponent fibers. Multicomponent fibers are fibers that have been formed from at least two polymer components. Such fibers are usually extruded from separate extruders but spun together to form one fiber. The polymers of the respective components are usually different from each other although multicomponent fibers may include separate components of similar or identical polymeric materials. The individual components are typically arranged in substantially constantly positioned distinct zones across the cross-section of the fiber and extend substantially along the entire length of the fiber. The configuration of such fibers may be, for example, a side-by-side arrangement, a pie arrangement, or any other arrangement. Multicomponent fibers and methods of making the same are taught in U.S. Pat. No. 5,108,820 to Kaneko, et al., U.S. Pat. No. 4,795,668 to Kruege, et al., U.S. Pat. No. 5,162,074 to Hills, U.S. Pat. No. 5,277,976 to Hogle, et al., U.S. Pat. No. 5,336,552 to Strack, et al., U.S. Pat. No. 5,466,410 to Hills, U.S. Pat. No. 5,069,970 to Largman, et al., U.S. Pat. No. 5,057,368 to Largman, et al., U.S. Pat. No. 5,382,400 to Pike, et al., and U.S. Pat. No. 5,989,004 to Cook, which are incorporated herein in their entirety by reference thereto for all purposes.

When utilized, multicomponent fibers can also be splittable. In fabricating multicomponent fibers that are splittable, the individual segments that collectively form the unitary multicomponent fiber are contiguous along the longitudinal direction of the multicomponent fiber in a manner such that one or more segments form part of the outer surface of the unitary multicomponent fiber. In other words, one or more segments are exposed along the outer perimeter of the multicomponent fiber. For example, splittable multicomponent fibers and methods for making such fibers are described in U.S. Pat. No. 5,935,883 to Pike and U.S. Pat. No. 6,200,669 to Marmon, et al., which are incorporated herein in their entirety by reference thereto for all purposes.

The substrate can also contain a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes.

In addition, the substrate can also be formed from a material that is imparted with texture one or more surfaces. For instances, in some embodiments, the substrate can be formed from a dual-textured spunbond or meltblown material, such as described in U.S. Pat. No. 4,659,609 to Lamers, et al. and U.S. Pat. No. 4,833,003 to Win, et al., which are incorporated herein in their entirety by reference thereto for all purposes.

Regardless of the materials or processes utilized to form the substrate, it is typically desired that the basis weight of the substrate be from about 20 to about 200 grams per square meter (gsm), and in some embodiments, between about 35 to about 100 gsm. Lower basis weight products may be particularly well suited for use as light duty substrates, while higher basis weight products may be better adapted for use as industrial substrates.

Because many of the substrates described above utilize nonwoven fabrics prepared from inherently hydrophobic (i.e., non-wettable) materials, it is often desired that the surface(s) of the fabrics be rendered more hydrophilic (i.e., wettable) so that the wiping solution can be more readily absorbed by the substrate. For instance, the substrate may be sprayed or coated with a surfactant solution during or after its formation. Once the substrate dries, the surfactant remains thereon until exposure to the wiping solution. Alternatively, a surfactant can be included in the fibrous or polymeric material of the substrate. By containing a surfactant, the resulting substrate can become more wettable so that the aqueous wiping solution is more easily absorbed by the substrate. It should be understood, however, that other well-known methods for increasing the wettability of a surface can also be used in the present disclosure.

The substrate may be applied with a wiping solution, which is described in more detail below, by any suitable method known in the art, such as spraying, dipping, saturating, impregnating, brush coating and the like. The amount of the wiping solution that may be added to the substrate may vary depending upon the type of substrate material utilized, the type of container used to store the substrates, the nature of the wiping solution, and the desired end use of the substrates. Generally, each substrate contains from about 150 to about 600 weight percent and desirably from about 300 to about 500 weight percent of the wiping solution based on the dry weight of the substrate.

As described above, in accordance with the present disclosure, the liquid absorbent substrate contains one or more odor control agents. Any of a variety of odor control particles may be used in accordance with the present disclosure that are capable of imparting odor control. For example, inorganic oxide particles, such as silica, alumina, zirconia, magnesium oxide, titanium dioxide, iron oxide, zinc oxide, copper oxide, zeolites, clays (e.g., smectite clay), combinations thereof, and so forth, may be employed in some embodiments of the present disclosure. Various examples of such inorganic oxide particles are described in U.S. Patent Application Publication Nos. 2003/0203009 to MacDonald; 2005/0084412 to MacDonald, et al.; 2005/0085144 to MacDonald, et al.; 2005/0084464 to McGrath, et al.; 2005/0084474 to Wu, et al.; 2005/0084438 to Do, et al.; and 2006/0008442 to MacDonald, et al., which are incorporated herein in their entirety by reference thereto for all purposes.

The inorganic oxide particles may possess various forms, shapes, and sizes depending upon the desired result. For instance, the particles may be in the shape of a sphere, crystal, rod, disk, tube, string, etc. If desired, the particles may be relatively nonporous or solid. That is, the particles may have a pore volume that is less than about 0.5 milliliters per gram (ml/g), in some embodiments less than about 0.4 milliliters per gram, in some embodiments less than about 0.3 ml/g, and in some embodiments, from about 0.2 ml/g to about 0.3 ml/g. The average size of the particles is generally less than about 500 microns, in some embodiments less than about 100 microns, in some embodiments less than about 100 nanometers, in some embodiments from about 1 to about 50 nanometers, in some embodiments from about 2 to about 50 nanometers, and in some embodiments, from about 4 to about 20 nanometers. As used herein, the average size of a particle refers to its average length, width, height, and/or diameter. The particles may have a surface area of from about 25 square meters per gram ($m^2/g$) to about 1000 $m^2/g$. In one embodiment, for instance, the surface area of the particles may be from about 50 $m^2/g$ to about 300 $m^2/g$. For example, particularly good odor removal properties have been found at surface areas of from about 25 $m^2/g$ to about 150 $m^2/g$. Surface area may be determined by the physical gas adsorption (B.E.T.) method of Bruanauer, Emmet, and Teller, Journal of American Chemical Society, Vol. 60, 1938, p. 309, with nitrogen as the adsorption gas.

The "zeta potential" of the particles may also vary as desired. For example, the particles may possess a negative zeta potential, such as less than about 0 millivolts (mV), in some embodiments less than about −10 mV, and in some embodiments, less than about −20 mV. Commercially available examples of particles having a negative zeta potential include Snowtex-C, Snowtex-O, Snowtex-PS, and Snowtex-OXS, which are silica nanoparticles available from Nissan Chemical of Houston, Tex. Alternatively, the particles may have a zeta potential of greater than about +20 millivolts (mV), in some embodiments greater than about +30 mV, and in some embodiments, greater than about +40 mV. By possessing a positive surface charge, the particles are well suited for being affixed to fibers that carry a negative surface charge (e.g., cellulosic fibers) through ionic attraction. Depending upon the difference in charge between the particles and the surface of the fibers (including van der Waals forces), the bond in some applications may be relatively permanent and substantive. Consequently, the particles may be affixed to fibers without the use of chemical binders or other attachment structures.

A positive zeta potential may be imparted to the particles of the present disclosure in a variety of different ways. In one embodiment, the particles are formed entirely from a positively charged material. For example, alumina particles may be used for odor reduction in accordance with the present disclosure. Some suitable alumina particles are described in U.S. Pat. No. 5,407,600 to Ando, et al., which is incorporated herein in its entirety by reference thereto for all purposes. Further, examples of commercially available alumina particles include, for instance, Aluminasol 100, Aluminasol 200, and Aluminasol 520, which are available from Nissan Chemical Industries Ltd. Alternatively, the positive zeta potential may be imparted by a continuous or discontinuous coating present on the surface of a core material. In some instances, these particles may actually possess a better stability over various pH ranges than particles formed entirely from positively charged materials. In one particular embodiment, for example, the particles are formed from silica particles coated with alumina. A commercially available example of such alumina-coated silica particles is Snowtex-AK, which is available from Nissan Chemical of Houston, Tex.

The inorganic oxide particles may also be modified with one or more transition metals to improve their odor control properties. More specifically, without being limited by theory, it is believed that the transition metal provides one or more active sites for capturing and/or neutralizing a malodorous compound. The active sites may be free, or may be weakly bound by water molecules or other ligands so that they are replaced by a malodorous molecule when contacted therewith. In addition, the particles still have the large surface area that is useful in adsorbing other malodorous compounds. Examples of some suitable transition metals that may be used in the present disclosure include, but are not limited to manganese, iron, cobalt, nickel, copper, zinc and so forth. Single metallic, as well as dinuclear, trinuclear, and cluster systems may be used.

The transition metal may be applied to the particles in a variety of ways. For instance, particles may simply be mixed with a solution containing the appropriate transition metal in the form of a salt, such as those containing a copper ion ($Cu^{+2}$), iron (III) ion ($Fe^{+3}$), manganese ion ($Mn^{2+}$), cobalt ion ($Co^{2+}$) and so forth. Such solutions are generally made by dissolving a metal salt in a solvent resulting in free metal ions in the solution. Generally, the metal ions are drawn to and adsorbed onto the particles due to their electric potential differences, i.e., they form an "ionic" bond. In many instances, however, it is desired to further increase the strength of the bond formed between the metal and particles, e.g., to form a coordinate and/or covalent bond. Although ionic bonding may still occur, the presence of coordinate or covalent bonding may have a variety of benefits, such as reducing the likelihood that any of the metal will remain free during use (e.g., after washing). Further, a strong adherence of the metal to the particles also optimizes odor adsorption effectiveness.

If desired, more than one type of transition metal may be bound to a particle. This has an advantage in that certain metals may be better at removing specific malodorous compounds than other metals. Likewise, different types of modified particles may be used in combination for effective removal of various malodorous compounds. In one embodiment, for instance, copper-modified silica particles are used in combination with manganese-modified silica particles. By using two different modified particles in combination, numerous malodorous compounds may be more effectively removed. For example, the copper-modified particle may be more effective in removing sulfur and amine odors, while the manganese-modified particle may be more effective in removing carboxylic acids. The ratio of the transition metal to the particles may be selectively varied to achieve the desired results.

For example, the transition metal to inorganic oxide particle ratio may be from about 5:1 to about 200:1. In one particular embodiment, for instance, the transition metal to inorganic oxide particle ratio may be from about 10:1 to about 75:1, such as from about 25:1 to about 75:1.

In addition to inorganic oxide particles, other particulate odor control agents may be employed in the present disclosure. For example, a quinone powder having odor control characteristics may also be used in the present disclosure.

Quinone powders may be prepared by drying a quinone compound in an oven and then converting the dried material to a powder using a milling device, such as a ball mill, bead mill, vibratory mill, sand mill, colloid mill, etc. Suitable dispersing agents may be, for example, condensation products of naphthalene sulfonic acid and formaldehyde, lignosulfonates or nonionic and anionic surface-active compounds. The resulting powder generally has an average particle size of from about 0.01 microns to about 20 microns, in some embodiments from about 0.5 microns to about 10 microns, and in some embodiments, from about 0.03 microns to about 6 microns. As used herein, the average size of a particle refers to its average length, width, height, and/or diameter. Some suitable anthraquinone powders are commercially available from Noveon Hilton Davis, Inc. of Cincinnati, Ohio and Sigma-Aldrich Chemical Co., Inc. of St. Louis, Mo.

Generally speaking, quinones refer to a class of compounds that possess a quinoid ring, such as anthraquinones, naphthaquinones, benzoquinones, hydroquinones, and so forth. Anthraquinones, for instance, have the following general formula:

The numbers 1-8 shown in the general formula represent a location on the fused ring structure at which substitution of a functional group may occur. Some examples of such functional groups that may be substituted on the fused ring structure include halogen groups (e.g., chlorine or bromine groups), sulfonyl groups (e.g., sulfonic acid salts), alkyl groups, benzyl groups, amino groups (e.g., primary, secondary, tertiary, or quaternary amines), carboxy groups, cyano groups, hydroxy groups, phosphorous groups, etc. Functional groups that result in an ionizing capability are often referred to as "chromophores." Substitution of the ring structure with a chromophore causes a shift in the absorbance wavelength of the compound. Thus, depending on the type of chromophore (e.g., hydroxyl, carboxyl, amino, etc.) and the extent of substitution, a wide variety of quinones may be formed with varying colors and intensities. Other functional groups, such as sulfonic acids, may also be used to render certain types of compounds (e.g., higher molecular weight anthraquinones) water-soluble.

Anthraquinone compounds may be classified for identification by their Color Index (CI) number, which is sometimes called a "standard." For instance, some suitable anthraquinones that may be used in the present disclosure, as classified by their "CI" number, include Acid Black 48, Acid Blue 25 (D&C Green No. 5), Acid Blue 40, Acid Blue 41, Acid Blue 45, Acid Blue 80, Acid Blue 129, Acid Green 25, Acid Green 27, Acid Green 41, Acid Violet 43, Mordant Red 11 (Alizarin), Mordant Black 13 (Alizarin Blue Black B), Mordant Red 3 (Alizarin Red S), Mordant Violet 5 (Alizarin Violet 3R), Alizarin Complexone, Natural Red 4 (Carminic Acid), Disperse Blue 1, Disperse Blue 3, Disperse Blue 14, Natural Red 16 (Purpurin), Natural Red 8, Reactive Blue 2 (Procion Blue HB), Reactive Blue 19 (Remazol Brilliant Blue R); and so forth. The structures of Acid Blue 25, Acid Green 41, Acid Blue 45, Mordant Violet 5, Acid Blue 129, Acid Green 25, and Acid Green 27 are set forth below:

Acid Blue 25

Acid Green 41

Acid Blue 45

Mordant Violet 5

Acid Blue 129

Acid Green 25

Acid Green 27

As stated above, other quinones may also be used in the present disclosure. For example, naphthaquinones may be used that have the following general formula:

The locations 1-6 of the naphthaquinone compounds may be substituted with functional groups in the manner described above. For instance, suitable examples of naphthaquinone compounds that may be used in the present disclosure include 1,4 naphthaquinone and 1,2 naphthaquinone, which have the following structures:

1,4-Naphthaquinone 1,2-Naphthaquinone

Without intending to be limited by theory, it is believed that the odor caused by many compounds is eliminated by the transfer of electrons to and/or from the malodorous compound. Specifically, oxidation of malodorous compounds via a reduction/oxidation ("redox") reaction is believed to inhibit the production of the characteristic odor associated therewith. The discovery that certain quinone compounds are able to eliminate odor is believed to be due to their ability to function as an oxidizing agent in a redox reaction. Many common malodorous compounds (e.g., ethyl mercaptan) are capable of being oxidized (i.e., donate electrons) via a redox reaction. Upon oxidation, the odors associated with such compounds are often eliminated or at least lessened. It is also believed that the reduction of the quinone compound via the redox reaction is readily reversible, and thus the reduced quinone compound may be oxidized by any known oxidizing agent (e.g., oxygen, air, etc.). The reduction/oxidation reactions are rapid and may take place at room temperature. Thus, although the odor control mechanism may consume the quinone compounds, they may simply be regenerated by exposure to air. Thus, long-term odor control may be achieved without significantly affecting the ability of the quinone compound to impart the desired color.

In addition to their ability to oxidize malodorous compounds, the chemical structure of certain quinone compounds may help improve odor elimination. For example, anthraquinone compounds that have at least one unsubstituted ring may result in better odor inhibition than those that are substituted at each ring with a functional group. Interestingly, anthraquinone compounds that are unsubstituted at the "first" ring (i.e., positions 5 through 8) appear to be particularly effective in reducing odor. Suitable examples of anthraquinone compounds that are unsubstituted at locations at their first ring include, but are not limited to, Acid Blue 25, Acid Blue 129, Acid Green 25, and Acid Green 27, the structures of which are set forth above. Other exemplary odor control quinone compounds are described in U.S. Patent Application Publication No. 2005/0131363 to MacDonald, et al., which is incorporated herein in its entirety by reference thereto for all purposes.

In addition to inorganic oxide particles and quinone compounds, in still another embodiment, the odor control agent may comprise activated carbon particles. The activated carbon particles, for instance, may have a particle size of from about 100 microns to about 5000 microns.

Activated carbon particles that may be used in the present disclosure can be obtained from numerous commercial sources. For instance, activated carbon particles are available from the Calgon Carbon Corporation of Pittsburgh, Pa., USA, under the trade name CARBABSORB®, from Sigma-Aldrich Chemical Company of Milwaukee, Wis., USA and from Cabot Corporation of Boston, Mass., USA.

Specific examples of activated carbon powder products that can be used include:
Activated carbon, Darco, 4-12 mesh (4760 to 1680 micron)
Activated carbon, Darco, 12-20 mesh (1680 to 841 micron)
Activated carbon, Darco, 20-40 mesh (841 to 400 micron)

Activated carbon, Darco, G-60, 100 mesh (149 micron)

Activated carbon, Darco, KB, 100 mesh (149 micron) wet powder

In addition, activated carbon powders incorporated into a binder may also be used. These activated carbon inks are described in patent publications US20050113771 by MacDonald, et al; US20060137568 by MacDonald et al; US20060140902 by MacDonald et al which are incorporated herein in there entirety by reference thereto for all purposes. These activated carbon inks may be applied via dip and squeeze for full coverage or be printed via gravure, flexographic or other printing techniques known to those skilled in the art. The activated carbon printed in this manner may be of pattern or grid or design or logo allowing aesthetic or otherwise visually pleasing designs to be made. In addition, the activated carbon may be one color of several applied to the wipe to allow for multiple colors where the activated carbon black color is used as a bold enhancer for the other primary colors used.

The amount of odor control agent present on the substrate can vary depending upon the particular application and the desired result. For instance, greater amounts of the odor control agent may be needed if the odor control agent is to be transferred to an adjacent surface. The amount can also vary depending upon the particular odor control agent selected.

In one embodiment, for instance, the odor control agent can be present on the substrate in an amount of at least 80 milligrams, such as from about 100 milligrams to about 2000 milligrams, such as from about 100 milligrams to about 500 milligrams.

The amount of odor control agent incorporated into the pre-moistened wipe can also be based upon the dry weight of the substrate. For instance, in one embodiment, the odor control agent can be present in the product in an amount from about 2% to about 30% by weight, based upon the dry weight of the substrate, such as from about 10% to about 30% by weight.

Of particular advantage, it has been discovered that the odor control agents described above can be combined into the wiping solution and applied to the liquid absorbent substrate instead of having to be incorporated into the liquid absorbent substrate separately from the wiping solution. Also of advantage, it has been found that the above described odor control agents can continue to reduce malodors even in a wet state. The odor control agents, for instance, can form a suspension within the wiping solution. Even when contained within a suspension, the odor control agents are capable of reducing malodors. As will be described in more detail below, the odor control agents can also be configured to be transferred to an adjacent surface when the liquid absorbent substrate is contacted with the surface.

When combining the odor control agents with other ingredients in the wiping solution, however, the other ingredients need to be carefully selected so that they do not interfere with the ability of the odor control agents to absorb and/or reduce malodors. For example, for many applications, the use of nonionic ingredients and components may better preserve the properties of the odor control agents. Anionic and cationic components may be present in some applications, however. The present inventors have discovered that, in one embodiment, the wiping solution should be substantially free of cationic components. For instance, in one particular embodiment, the wiping solution is substantially free of any cationic surfactants. As will be described in greater detail below, fragrances incorporated into the wiping solution must also be carefully selected to ensure their compatibility with the odor control agents.

The following is a list of components and ingredients that may be contained in the wiping solution.

Surfactant

One or more surfactants may be contained in the wiping solution. Any surfactants present within the wiping solution, however, should be carefully selected so as to not interfere with the odor control properties of the odor control agent. Surfactants, when present, can generally increase the wettability of the substrate and can also improve the ability of the wiping solution to clean surfaces.

In general, surfactants that may be present in the wiping solution include nonionic surfactants and some selected anionic surfactants. In one embodiment, however, the wiping solution is substantially free of cationic surfactants and/or amphoteric surfactants. Cationic surfactants, for instance, can adversely interfere with the odor control agents.

Nonionic surfactants typically have a hydrophobic base, such as a long chain alkyl group or an alkylated aryl group, and a hydrophilic chain comprising a certain number (e.g., 1 to about 30) of ethoxy and/or propoxy moieties. Examples of some classes of nonionic surfactants that can be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, and mixtures thereof.

Specific examples of various nonionic surfactants that may be used in the wiping solution include polyoxyethylene sorbitan monolaurate which is referred to as polysorbate 20, glycerin, lauric acid, castor oil, myristic acid, oleic acid, stearyl alcohol, and cetyl alcohol. The myristic acid and oleic acid can be present in a hydrogenated form which provides the nonionic character.

Other specific examples of suitable nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG 600 dioleate, PEG 400 dioleate, and mixtures thereof.

Additional nonionic surfactants that can be used include water soluble alcohol ethylene oxide condensates are the condensation products of a secondary aliphatic alcohol containing between about 8 to about 18 carbon atoms in a straight or branched chain configuration condensed with between about 5 to about 30 moles of ethylene oxide. Such nonionic surfactants are commercially available under the trade name Tergitol® from Union Carbide Corp., Danbury, Conn. Specific examples of such commercially available nonionic surfactants of the foregoing type are $C_{11}$-$C_{15}$ secondary alkanols condensed with either 9 moles of ethylene oxide (Tergitol® 15-S-9) or 12 moles of ethylene oxide (Tergitol® 15-S-12) marketed by Union Carbide Corp., (Danbury, Conn.).

Other suitable nonionic surfactants include the polyethylene oxide condensates of one mole of alkyl phenol containing from about 8 to 18 carbon atoms in a straight- or branched chain alkyl group with about 5 to 30 moles of ethylene oxide. Specific examples of alkyl phenol ethoxylates include nonyl condensed with about 9.5 moles of ethylene oxide per mole of nonyl phenol, dinonyl phenol condensed with about 12 moles of ethylene oxide per mole of phenol, dinonyl phenol condensed with about 15 moles of ethylene oxide per mole of phenol and diisoctylphenol condensed with about 15 moles of ethylene oxide per mole of phenol. Commercially available nonionic surfactants of this type include Igepal® CO-630 (a nonyl phenol ethoxylate) marketed by ISP Corp. (Wayne, N.J.). Suitable non-ionic ethoxylated octyl and nonyl phenols include those having from about 7 to about 13 ethoxy units. Such compounds are commercially available under the trade name Triton® X (Union Carbide, Danbury Conn.).

Alkyl polyglycosides may also be used as a nonionic surfactant in the present inventive compositions. Suitable alkyl polyglycosides are known nonionic surfactants that are alkaline and electrolyte stable. Alkyl mono and polyglycosides are prepared generally by reacting a monosaccharide, or a compound hydrolyzable to a monosaccharide with an alcohol such as a fatty alcohol in an acid medium.

One example of such alkyl polyglycosides is APG™ 325 CS GLYCOSIDE, which is described as being a 50% $C_9$-$C_{11}$ alkyl polyglycoside, also commonly referred to as D-glucopyranoside. Another example of an alkyl polyglycoside surfactant is GLUCOPON™ 625 CS, which is described as being a 50% $C_{10}$-$C_{16}$ alkyl polyglycoside, also commonly referred to as a D-glucopyranoside. Both APG™ 325 CS GLYCOSIDE and GLUCOPON™ 625 CS are commercially available from Henkel Corp., Ambler Pa.

Other useful nonionic surfactants include compositions based on amine oxides. One general class of useful amine oxides include alkyl di(lower alkyl) amine oxides in which the alkyl group has about 10-20, and preferably 12-16 carbon atoms, and can be straight or branched chain, saturated or unsaturated. The lower alkyl groups include between 1 and 7 carbon atoms. Examples include lauryl, dimethyl amine oxide, myristyl dimethyl amine oxide, and those in which the alkyl group is a mixture of different amine oxide, dimethyl cocoamine oxide, dimethyl (hydrogenated tallow) amine oxide, and myristyl/palmityl dimethyl amine oxide.

Another class of useful amine oxides include alkyl di(hydroxy lower alkyl) amine oxides in which the alkyl group has about 10-20, and particularly 12-16 carbon atoms, and can be straight or branched chain, saturated or unsaturated. Examples are bis(2-hydroxyethyl) cocoamine oxide, bis(2-hydroxyethyl) tallow amine oxide, and bis(2-hydroxyethyl) stearylamine oxide. Moreover, still other useful amine oxides include those characterized as alkylamidopropyl di(lower alkyl) amine oxides, in which the alkyl group has about 10-20 carbon atoms, and can be straight or branched chain, saturated or unsaturated. Examples are cocoamidopropyl dimethyl amine oxide and tallowamidopropyl dimethyl amine oxide.

Additional useful amine oxides include alkylmorpholine oxides in which the alkyl group has about 10-20 carbon atoms, and can be straight or branched chain, saturated or unsaturated. Further examples of amine oxides include those that commercially under the trade name AMMONYX (Stepan Co., Chicago Ill.).

In certain instances, it may also be desirable to utilize one or more anionic surfactants within the wiping solution. Any anionic surfactant present within the solution, however, should be carefully selected so as to not interfere with the odor control agent. Examples of anionic surfactants that may be used include potassium laureth phosphate, capric acid, stearic acid, erucic acid, and the de-hydrogenated forms of myristic acid, oleic acid, and lauric acid.

Other suitable anionic surfactants include, but are not limited to, alkyl sulfates, alkyl ether sulfates, alkyl ether sulfonates, sulfate esters of an alkylphenoxy polyoxyethylene ethanol, alpha-olefin sulfonates, beta-alkoxy alkane sulfonates, alkylauryl sulfonates, alkyl monoglyceride sulfates, alkyl monoglyceride sulfonates, alkyl carbonates, alkyl ether carboxylates, fatty acids, sulfosuccinates, sarcosinates, octoxynol or nonoxynol phosphates, taurates, fatty taurides, fatty acid amide polyoxyethylene sulfates, isethionates, or mixtures thereof.

Particular examples of some suitable anionic surfactants include, but are not limited to, $C_8$-$C_{18}$ alkyl sulfates, $C_8$-$C_{18}$ fatty acid salts, $C_8$-$C_{18}$ alkyl ether sulfates having one or two moles of ethoxylation, $C_8$-$C_{18}$ alkamine oxides, $C_8$-$C_{18}$ alkoyl sarcosinates, $C_8$-$C_{18}$ sulfoacetates, $C_8$-$C_{18}$ sulfosuccinates, $C_8$-$C_{18}$ alkyl diphenyl oxide disulfonates, $C_8$-$C_{18}$ alkyl carbonates, $C_8$-$C_{18}$ alpha-olefin sulfonates, methyl ester sulfonates, and blends thereof. The $C_8$-$C_{18}$ alkyl group can be straight chain (e.g., lauryl) or branched (e.g., 2-ethylhexyl). The cation of the anionic surfactant can be an alkali metal (e.g., sodium or potassium), ammonium, $C_1$-$C_4$ alkylammonium (e.g., mono-, di-, tri), or $C_1$-$C_3$ alkanolammonium (e.g., mono-, di-, tri).

Specific examples of such anionic surfactants include, but are not limited to, lauryl sulfates, octyl sulfates, 2-ethylhexyl sulfates, lauramine oxide, decyl sulfates, tridecyl sulfates, cocoates, lauroyl sarcosinates, lauryl sulfosuccinates, linear $C_{10}$ diphenyl oxide disulfonates, lauryl sulfosuccinates, lauryl ether sulfates (1 and 2 moles ethylene oxide), myristyl sulfates, oleates, stearates, tallates, ricinoleates, cetyl sulfates, and similar surfactants.

Fragrances

In addition to the surfactants, any fragrances contained within the wiping solution should be carefully selected. Fragrances, for instance, are prone to interfere with the odor control agents. Thus, in one embodiment, the wiping solution may be fragrance free.

Fragrances that may be used in the wiping solution include non-hetero atom containing fragrances. Such fragrances include hydrocarbon fragrances. Particular examples of fragrances that may be used in the wiping solution include terpenes, such as limonene, pinene, menthol, camphor, and mixtures thereof.

Sequestrant

In one embodiment, the wiping solution may contain a sequestrant. A sequestrant is a substance whose molecules can form one or more bonds with a metal ion. In particular, water often contains metal ions, such as calcium ions, that might react with anionic components (e.g., surfactants, acids, etc.) present within the wiping solution. Without being limited by theory, it is believed that a sequestrant can form a complex with such metal ions so that the remaining anionic components are capable of fulfilling their desired function. For example, in one embodiment, a surfactant that remains substantially unreacted with metal ions can better function as a cleansing agent. Moreover, in some instances, it is also believed that the sequestrant can further improve the ability of the wiping solution to inhibit the growth of gram negative and/or gram positive bacteria.

Some examples of sequestrants that may be used in the wiping solution of the present disclosure include, but are not limited to, ethylenediamines, ethylenediaminetetraacetic acids (EDTA) acid and/or salts thereof, citric acids and/or salts thereof, glucuronic acids and/or salts thereof, polyphosphates, organophosphates, dimercaprols, and the like.

The amount of the sequestrant utilized in the wiping solution can generally vary depending on the relative amounts of the other components present within the solution. Typically, when utilized, the sequestrant is present in the solution in an amount between about 0.01% to about 5% by weight, in some embodiments between about 0.01 to about 1.5% by weight, and in some embodiments, between about 0.1% to about 1% by weight of the wiping solution.

Preservatives

In some embodiments, the wiping solution can also contain one or more preservatives. Although not required, preservatives can inhibit the growth of microorganisms on the premoistened wiper.

Some suitable preservatives that can be used in the present disclosure include, but are not limited to, Kathon CG®, which is a mixture of methylchloroisothiazolinone and methylisothiazolinone available from Rohm & Haas; Mackstat H 66 (available from McIntyre Group, Chicago, Ill.); DMDM hydantoin (e.g., Glydant Plus, Lonza, Inc., Fair Lawn, N.J.); iodopropynyl butylcarbamate; benzoic esters (parabens), such as methylparaben, propylparaben, butylparaben, ethylparaben, isopropylparaben, isobutylparaben, benzylparaben, sodium methylparaben, and sodium propylparaben; 2-bromo-2-nitropropane-1,3-diol; benzoic acid; amidazolidinyl urea; diazolidinyl urea; and the like. Other suitable preservatives include those sold by Sutton Labs, such as "Germall 115" (amidazolidinyl urea), "Germall II" (diazolidinyl urea), and "Germall Plus" (diazolidinyl urea and iodopropynyl butylcarbonate).

When utilized, the amount of the preservative utilized in the wiping solution can generally vary depending on the relative amounts of the other components present within the solution. For example, in some embodiments, the preservative is present in the solution in an amount between about 0.001% to about 5% by weight, in some embodiments between about 0.001 to about 1% by weight, and in some embodiments, between about 0.1% to about 0.15% by weight of the wiping solution.

pH Modifiers

In general, the pH of the wiping solution may be controlled to be within any desired range. If necessary, various pH modifiers may be utilized in the wiping solution to achieve the desired pH level. For instance, some examples of basic pH modifiers that may be used in the present disclosure include, but are not limited to, ammonia; mono-, di-, and tri-alkyl amines; mono-, di-, and tri-alkanolamines; alkali metal and alkaline earth metal hydroxides; alkali metal and alkaline earth metal silicates; and mixtures thereof. Specific examples of basic pH modifiers are ammonia; sodium, potassium, and lithium hydroxide; sodium, potassium, and lithium meta silicates; monoethanolamine; triethylamine; isopropanolamine; diethanolamine; and triethanolamine.

Moreover, some examples of acidic pH modifiers that may be used in the present disclosure include, but are not limited to, mineral acids; and carboxylic acids; and polymeric acids. Specific examples of suitable mineral acids are hydrochloric acid, nitric acid, phosphoric acid, and sulfuric acid. Specific examples of suitable carboxylic acids are citric acid, glycolic acid, lactic acid, maleic acid, malic acid, succinic acid, glutaric acid, benzoic acid, malonic acid, salicylic acid, gluconic acid, and mixtures thereof. Specific examples of suitable polymeric acids include straight-chain poly(acrylic) acid and its copolymers (e.g., maleic-acrylic, sulfonic-acrylic, and styrene-acrylic copolymers), cross-linked polyacrylic acids having a molecular weight of less than about 250,000, poly (methacrylic) acid, and naturally occurring polymeric acids such as carageenic acid, carboxymethyl cellulose, and alginic acid.

When utilized, the amount of the pH modifier can be present in any effective amount needed to achieve the desired pH level. For example, in some embodiments, the pH modifier is present in the formulation in an amount between about 0.001% to about 5% by weight, in some embodiments between about 0.001 to about 1% by weight, and in some embodiments, between about 0.1% to about 0.25% by weight of the wiping solution. In particular embodiments, the pH modifier contains an alkali metal silicate (e.g., sodium meta silicate) and an alkali metal hydroxide (e.g., sodium hydroxide) such that the silicate is present in an amount of between about 0.001% to about 0.2% by weight of the wiping solution and the hydroxide is present in an amount of between about 0.001 to about 0.05% by weight of the wiping solution.

Carrier

One or more carriers may also be present within the wiping solution. In one embodiment, for instance, the carrier may comprise water. Typically, water can be present in the wiping solution in an amount from about 1% to about 99% by weight, such as from about 60% to about 99% by weight.

Non-aqueous carriers may also be used. Examples of some suitable non-aqueous carriers include, but are not limited to, glycols, such as propylene glycol, butylene glycol, triethylene glycol, hexylene glycol, polyethylene glycols, ethoxydiglycol, and dipropyleneglycol; alcohols, such as ethanol, n-propanol, and isopropanol; triglycerides; ethyl acetate; acetone; triacetin; and combinations thereof. Especially desired solvent combinations include a glycol, particularly hexylene and/or propylene glycol, and one or more lower alcohols, particularly isopropanol, n-propanol, and/or ethanol.

Non-aqueous solvents may be present alone or in combination with water. When present, the non-aqueous carrier can be present in an amount from about 0.01% to about 30% by weight.

Other Optional Ingredients

In order to better enhance the benefits to consumers, other optional ingredients can also be used. For instance, some classes of ingredients that can be used include, but are not limited to: antioxidants (product integrity) such as tocopheryl acetate; skin agents, such as aloe extract; astringents—cosmetic (induce a tightening or tingling sensation on skin); astringents—drug (a drug product which checks oozing, discharge, or bleeding when applied to skin or mucous membrane and works by coagulating protein); biological additives (enhance the performance or consumer appeal of the product); colorants (impart color to the product); deodorants (reduce or eliminate unpleasant odor and protect against the formation of malodor on body surfaces); external analgesics (a topically applied drug that has a topical analgesic, anesthetic, or antipruritic effect by depressing cutaneous sensory receptors, of that has a topical counterirritant effect by stimulating cutaneous sensory receptors); film formers (to hold active ingredients on the skin by producing a continuous film on skin upon drying); fragrances (consumer appeal); hydrotropes (helps dissolve some antimicrobial agents); opacifiers (reduce the clarity or transparent appearance of the product); skin conditioning agents; skin exfoliating agents (ingredients that increase the rate of skin cell turnover such as alpha hydroxy acids and beta hydroxyl acids); skin protectants (a drug product which protects injured or exposed skin or mucous membrane surface from harmful or annoying stimuli); sunscreens (ingredients that absorb at least 85 percent of the light in the UV range at wavelengths from 290 to 320 nanometers, but transmit UV light at wavelengths longer than 320 nanometers); antimicrobial agents; and thickeners (to increase the viscosity of the formulation).

Once the wiping solution is formulated and impregnated into the liquid absorbent substrate, the substrate can be delivered to consumers in various forms. For instance, in one embodiment, the substrate can be provided in a continuous, perforated roll. In an alternative embodiment, the substrate can be provided in individual sheets that are stacked together.

Due to the presence of one or more odor control agents, the wiper of the present disclosure can have many useful applications in addition to simply wiping up spills and messes. For instance, in one embodiment, the wiper can be used as a delivery device for delivering the odor control agents to a surface. For example, the odor control agents can be incorporated into the wiper such that the odor control agent transfers to an adjacent surface when contacted with the wiper. The wiping solution can be released from the wiper and transferred to the surface containing the odor control agents.

In one embodiment, for instance, the odor control agents can be present as a suspension within the wiping solution. In this manner, as the wiping solution is transferred to an adjacent surface, the wiping solution carries the odor control agents with it. For instance, the pre-moistened wipe of the present disclosure can be configured so that from about 10% to about 50% of the wiping solution transfers to an adjacent surface when contacted with the surface. For instance, in one particular embodiment, from about 15% to about 30% of the wiping solution transfers to an adjacent surface.

The amount of odor control agent that is transferred to the adjacent surface during contact can vary depending upon various factors. In general, for instance, the odor control agent can transfer to an adjacent surface when contacted with the wipe in an amount from about 0.5 gsm to about 5 gsm or even higher. In one particular embodiment, for instance, from about 1 gsm to about 2 gsm of the odor control agent is transferred.

In addition to being a delivery device for an odor control agent, the wiper of the present disclosure can also be used to eliminate odors of particular objects, such as personal care articles. For instance, in one embodiment, the wiper can be configured to be used as a baby wipe. In this embodiment, the wiper can not only be used to wipe up urine and/or fecal matter off of a baby, but can also be used to reduce malodors not only on the baby but also residual odors that may be emitted from the dirty diaper.

For example, in one particular embodiment, a method of the present disclosure may include the steps of removing an absorbent article, such as a diaper, from a wearer. The absorbent article may be removed after being insulted with urine and/or fecal matter. The wiper of the present disclosure can be used to wipe off any remaining fecal matter or urine on the wearer. Odor control agents can be transferred to the wearer during this step.

After the wearer has been wiped with the wiper, the absorbent article can then be wrapped around the pre-moistened wipe for disposal. By wrapping the absorbent article around the pre-moistened wipe, the odor control agents present in the wiper can be used to reduce malodors given off by the absorbent article as the article is disposed of. For instance, the wiper can reduce malodors given off by the absorbent article while the absorbent article is in household trash and/or in outside garbage cans.

The present disclosure may be better understood with respect to the following examples.

Example 1

The following demonstrates the synthesis of CuOXS odor control solution. Snowtex OXS (50 mL, 5.4 g $SiO_2$ solids, $6.37 \times 10^{-5}$ mol $SiO_2$ particles (based on diameter 5 nm and density 2.27)) was transferred to a 1 L beaker containing a stir bar, and deionized water (150 mL) was added to the reaction beaker. With constant stirring, a solution of $CuCl_2.4H_2O$ (0.545 g, $3.19 \times 10^{-3}$ mol) in water (100 mL) was added to the reaction beaker. A solution of $NaHCO_3$ (8.4 g, 0.1 mol) in water (200 mL) was added to the reaction beaker with vigorous stirring. The blue suspension was allowed to stir for an additional 30 minutes. Synthesis of FeOXS, MnOXS and CoOXS followed the same procedure. $FeCl_3.6H_2O$, $MnCl_2.4H_2O$ and $CoCl_2.6H_2O$ were used, respectively; the appropriate amount was used to give a 50:1 metal ion to silica particle mole ratio.

Example 2

The following demonstrates the synthesis of a wiping solution. The odor control suspension (Example 1) was combined with a wiping solution that contained the following ingredients.

| Ingredient | % by Weight |
|---|---|
| Potassium Laureth Phosphate | 0.600 |
| Glycerin | 0.300 |
| Polysorbate 20 | 0.300 |
| Na-EDTA | 0.200 |
| DMDM Hydantoin | 0.200 |
| Methylparaben | 0.150 |
| *Aloe barbadensis* | 0.001 |
| Tocopheryl acetate | 0.001 |
| Malic acid | 0.070 |
| Water | 98.178 |

The amount of each suspension or solution used was adjusted to give a final concentration of 1.5% (wt/wt) odor control agent in the final wiping solution.

Example 3

The wiping solution formulated in Example 2 was then applied to a substrate for forming a pre-moistened wipe. The substrate comprised a coform material containing 70% by weight pulp and 30% by weight polypropylene meltblown fibers. The coform material was saturated with the wiping solution. In particular, the wiping solution was added to the coform material in an amount of 300% by weight. The resulting pre-moistened wipe contained the odor control agent in an amount of approximately 5% by weight based upon the dry weight of the substrate.

Example 4

Figure 1:
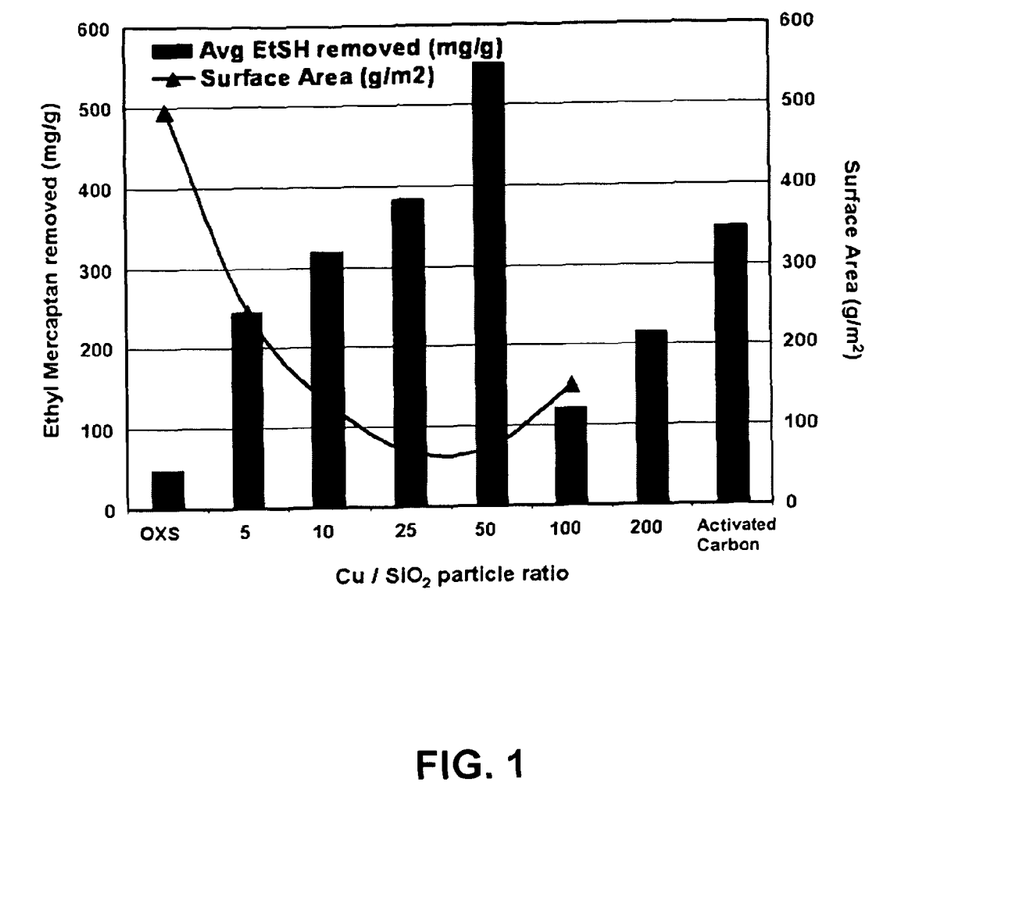
FIGS. 1 and 2 are graphical representations of some of the results contained in the examples below.

Powder samples of Cu modified silica particles were assessed for their ability to remove ethyl mercaptan using headspace gas chromatography (headspace GC) analysis. Varying Cu concentrations were assessed, and these were noted as Cu ion to silica particle ratio. For comparison, activated carbon particles were also assessed. Data collection was performed in triplicates, and odor removal is reported as milligram (mg) of ethyl mercaptan removed per gram (g) of powder sample. The results are illustrated in FIG. 1.

The system with Cu ions to silica particle ratio 50:1 was the most efficient at removing EtSH (~550 mg/g). In the range ratio zero to 50, there is a linear increase in EtSH removal that corresponds to an increase in copper content. Interestingly after this, there is a step reduction in EtSH removal (550 mg/g at ratio 50 drops to 110 mg/g at ratio 100). The appearance of the powdery product at ratio 50 is pale blue, while that at 100 is pale cyan to green. This indicates that the primary coordination sphere around copper is different between the two. Differences in the coordination sphere of copper lead to differences in the ligand-to-metal-charge-transfer (LMCT) band energy; this will directly affect the appearance of the material. It is suggested that the step reduction in EtSH removal capacity here is due to competitive reactions with sodium ions (source NaHCO3, base used in synthesis). When compared to the performance of activated carbon powder, the systems at 10, 25 and 50 Cu/silica ratio performed equally or better at removal of EtSH (see FIG. 1).

The headspace GC parameters are described below. The general procedures are as follow. A sample was inserted into a GC/headspace vial, ethyl mercaptan (EtSH, 2.4 µL) was added to each vial and immediately sealed. Sample vials were transferred to the headspace apparatus and headspace samples were automatically obtained by the GC unit. Data was collected using an automated sampler. All samples were made in triplicate. The GC/headspace column used was a model FFAP-CB (Chrompack, The Netherlands; Catalog No. 7485) 25 m, 0.32 mm ID, 0.3µ film. Parameters for the headspace unit are listed in Table 1.

TABLE 1

GC headspace parameters for all experiments.
GC-headspace parameters

| | | |
|---|---|---|
| Zone Temperatures, ° C. | Oven | 40 |
| | Loop | 85 |
| | TR. Line | 90 |
| Event Times, min | GC Cycle time | 12.0 |
| | Vial equilibration time | 10.0 |
| | Pressurization time | 0.20 |
| | Loop fill time | 0.20 |
| | Loop equilibration time | 0.15 |
| | Inject time | 0.30 |
| Vial Parameters | First vial | 1 |
| | Last vial | 1 |
| | Shake | [off] |

Referring to FIG. 1, the surface area of the odor control agent is also indicated by the line graph. As shown, lower surface areas generally increased odor removal capacity. For instance, the best odor removing samples had surface areas of less than about 200 g/m$^2$.

As also shown in FIG. 1, the activated carbon particles were also effective in odor removal.

Example 5

Powder samples of transition metal modified silica particles were assessed for their ability to remove ethyl mercaptan, triethylamine and isovaleraldehyde, respectively, using headspace GC analysis. Activated carbon powder was also assessed for comparison purposes. The transition metals used were Cu (CuCl$_2$.2H$_2$O), Fe (FeCl$_3$.6H$_2$O), Mn (MnCl$_2$.4H$_2$O) and Co (CoCl$_2$.6H$_2$O); and the metal concentration was set a 50:1 ratio (metal ion to silica particle).

The following results were obtained:

TABLE 2

Headspace GC data for transition metal ($Cu^{2+}$, $Fe^{3+}$, $Mn^{2+}$ or $Co^{2+}$) modified silica particles removal of ethyl mercaptan, triethylamine and isovaleraldehyde (mg odor removed per g sample).

| | Ethyl Mercaptan | Triethylamine | Isovaleradehyde |
|---|---|---|---|
| Cu | 461 | 87 | 2 |
| Fe | 85 | 258 | 10 |
| Mn | 58 | 47 | 430 |
| Co | 820 | Na | Na |
| Activated Carbon | 353 | 449 | 413 |

The data above shows each different metal modified silica system to be specifically stronger in removal of a thiol, an amine or an acid based organic compound. Co and Cu are more effective against ethyl mercaptan; Fe is more effective against triethylamine; and Mn is more effective against isovaleradehyde. Activated carbon was equally effective against all three classes of compound.

The headspace GC parameters and procedures are described in Example 3.

Example 6

Pre-moistened wipes were constructed in accordance with the present disclosure. The pre-moistened wipes comprised a liquid absorbent substrate containing a wiping solution. The wiping solution contained inorganic oxide particles modified with a transition metal, namely silicon dioxide particles modified with copper.

The silica particles used to form the odor control agent were SNOWTEX-OXS, which are colloidal silica nanoparticles commercially available from Nissan Chemical America of Houston, Tex. The particles have an average particle size of between 4 to 6 nanometers and a surface area between 200 to 500 square meters per gram as measured using the BET method. The silica particles were modified with copper. The copper to silica ratio was 25:1.

The absorbent substrate used comprised a coform material. The coform material had a basis weight of 66 gsm and contained 70% by weight wood pulp and 30% by weight polypropylene meltblown fibers. The wipes had a size of 19 cm×19 cm.

The wiping solution contained approximately 97% by weight water and 3% by weight other ingredients. In particular, the wiping solution contained the following:

TABLE 3

Composition of wiping solution, which is a mixture of the CuOXS odor control suspension and the Natural Care Unscented wet wipes solution.

| Ingredient | % by Weight |
|---|---|
| Potassium Laureth Phosphate | 0.600 |
| Glycerin | 0.300 |
| Polysorbate 20 | 0.300 |
| Na-EDTA | 0.200 |
| DMDM Hydantoin | 0.200 |
| Methylparaben | 0.150 |
| *Aloe barbadensis* | 0.001 |
| Tocopheryl acetate | 0.001 |
| Malic acid | 0.070 |
| Odor control agent | 1.500 |
| Water | 96.678 |

The wiping solution was fragrance free. The wiping solution was applied to the substrate in an amount of 300% by weight based upon the weight of the substrate.

To test the efficacy of the odor control agent when used in a pre-moistened wipe, testing was conducted using panelists for odor screening. The odorants used were aged human urine and black sea salt (sulfur odor to model feces). The testing was conducted on pre-moistened wipes by themselves in MASON jars (1 quart) and also pre-moistened wipes placed inside a diaper. In particular, the diaper was rolled up and placed in the MASON jars. The diapers were insulted with the odorants and the wet wipes were not. The samples were aged in an incubator for 12 hours and the jars assessed. In particular, a blind study was conducted with the panelists for odor levels. The panel members were asked to rank the odor on a scale of 1 (least or no odor) to 10 (most odor). The scores given by each panelist were combined with the other panelists' scores.

The control jars were comprised of pre-moistened wipes that did not contain the odor control agent.

In the first study, wet wipes were insulted with the aged urine (Table 4). Next, a study was completed that included insulted diapers (Table 5). The following results were obtained:

TABLE 4

Cumulative scores from a panel assessing the ability of wet wipes (control and with odor control agent) to remove urine odor.

| Sample | Urine Odor Assessment (3 panelists) |
| --- | --- |
| Wet wipe control | 30 |
| Wet wipe with odor control agent | 3 |
| Diaper control with wet wipe inside | 23 |
| Diaper with odor control agent wipe inside | 6 |

TABLE 5

Cumulative scores from a panel assessing the ability of wet wipes (control and with odor control agent) to remove sea salt odor (sulfur odor) from insulted diapers.

| Sample | Sulfur Odor Assessment (3 panelists) |
| --- | --- |
| Wet wipe control | 27 |
| Wet wipe with odor control agent | 6 |
| Control diaper with wet wipe inside | 18 |
| Diaper with odor control agent wipe inside | 3 |

As shown above, malodors were reduced when the odor control agent was present in the pre-moistened wipe. The above results show that the odor control agent is not only effective in working in a wet environment but also can significantly reduce malodors given off by soiled diapers.

Example 7

The ability to coat a quinone compound onto a paper towel was demonstrated. Specifically, D&C Green No. 5 was initially dissolved into 1 liter of deionized water to form five sample solutions (Samples 2-6), wherein the concentration of D&C Green No. 5 varied from 0.001 wt. %, 0.01 wt. %, 0.1 wt. %, 0.25 wt. %, and 0.5 wt. %, respectively. Each solution also contained 1 wt. % of Snowtex AK (SN-AK) particles, which are colloidal silica nanoparticles coated with alumina and commercially available from Nissan Chemical America of Houston, Tex. The particles have an average particle size of between 10 to 20 nanometers and a surface area between 180 to 240 square meters per gram. A solution of only 1 wt. % of SN-AK particles was also formed as a control (Sample 1). Scott® paper towels (commercially available from Kimberly-Clark Corp.) were weighed, oven-dried overnight at 90° C., and weighed again the next day to calculate the amount of residual water in each towel. The towels were then dipped into each solution and hung to dry overnight, after which they were weighed again. The treated towels were then rinsed in deionized water to remove any unbound dye and hung again to dry overnight. After weighing the treated towels, they were once again oven-dried overnight at 90° C. and weighed to determine the dry add-on percentages (100×[dry weight final/dry weight initial]).

The resulting add-on percentages for Samples 1-6 were 5.7%±1.8%, 4.8%±1.3%, 4.3%±0.9%, 7.0%±1.2%, 2.8%±0.8%, and 0.9%±0.8%, respectively. The difference between the add-on level of Sample 1 (the control sample) and Samples 2-3 (0.001 wt. % and 0.01 wt. % D&C Green No. 5) was not significant. The highest add-on was achieved for Sample 4, which utilized 0.1 wt. % D&C Green No. 5. However, the add-on level decreased in Samples 5-6 when the concentration of dye was further increased. Without intending to be limited by theory, it is believed that higher dye concentrations may make it more difficult for the SN-AK particles to bind to the paper towel. Thus, the coating contains more dye particles than SN-AK-bound dye particles, thereby resulting in a lighter towel and a lower add-on percentage. Nevertheless, because the dye particles weigh considerably less than the SN-AK particles, the add-on level of the dye alone is inherently difficult to calculate.

Example 8

The effectiveness of a quinone dye in reducing garlic odor was demonstrated. Initially, strips of each treated towel of Example 7 (Samples 2-6) were cut and placed in a jar with approximately 125 milligrams of freshly cut garlic. A strip from an uncoated Scott® paper towel (Sample 7), as well as the control towel of Example 1 (Sample 1), were also tested as controls. Garlic odor was assessed by a panel of individuals at intervals of 3, 19, 27, 41, and 121 hours. A score of "7" was assigned to the most malodorous jar and a score of "1" was assigned to the least malodorous jar. The results are shown in FIG. 2.

Figure 2:
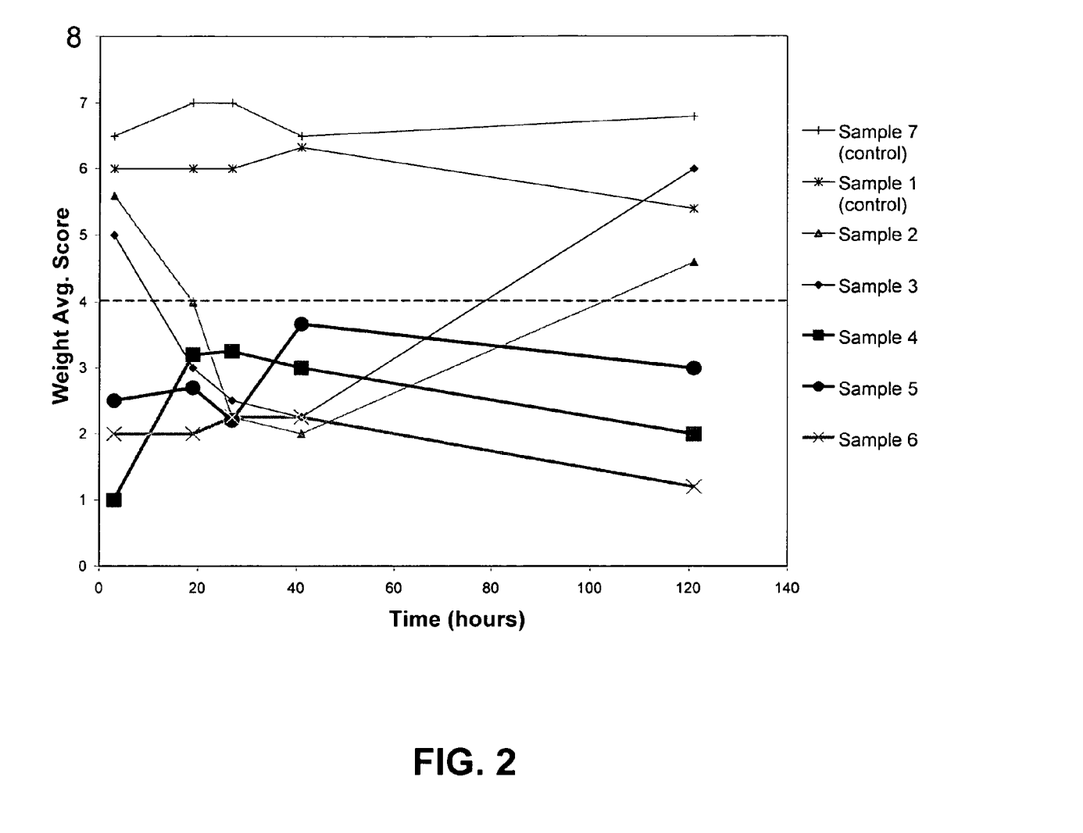

As shown, a line is drawn in FIG. 2 at the score of "4" to represent the level at which garlic malodor was perceived to be most dramatically reduced. The control samples did not reduce garlic odor and received almost unanimous scores of either 6 or 7. The dye concentrations of 0.1 wt. %, 0.25 wt. %, and 0.5 wt. % (Samples 4-6) were shown to be the most efficacious in removing garlic odor. The behavior of Samples 2-3 (0.001 wt. % and 0.01 wt. % D&C Green No. 5) was found to be time-dependent. Specifically, these treatments were not initially efficacious in removing garlic odor, but seemed to improve as time increased.

Example 9

To illustrate the utility of these pre-moistened wipes for surface cleaning and leaving a layer of odor absorbing coating on the cleaned surface, the following experiment was conducted. An identical set of pre-moistened wipes were prepared as follows. The absorbent substrate used comprised a coform material. The coform material had a basis weight of 66 gsm and contained 70% by weight wood pulp and 30% by weight polypropylene meltblown fibers. The wipes had a size of 19 cm×19 cm. The wiping solution contained 92% by weight water and 8% by weight other ingredients. In particular the wiping solution contained 5% by weight copper silica (25:1) along with the other ingredients described earlier in Table 3. The wiping solution was fragrance free. The wiping solution was applied to the substrate in an amount of 300% by weight based upon the weight of the substrate. The wipes were then used to wipe a bench-top surface measuring 1 meter by 1 meter square. The weight of each wipe was determined before wiping and after wiping. This experiment was performed six times and the results shown in Table 6 below. As can be seen from the results the wipes left the odor controlling formulation on the surface in the range of 1.2 to 1.7 g/m$^2$. Thus not only do the pre-moistened wipe clean off the surface contaminants they also leave behind a coating of odor controlling formulation on the cleaned surface for continued odor controlling properties.

TABLE 6

Quantification data of the amount of wiping solution left behind after the wiping process.

| Wipe weight before (g) | Wipe weight after (g) | Deposited amount of surface (g/m$^2$) |
|---|---|---|
| 7.7031 | 6.4459 | 1.26 |
| 7.9810 | 6.6731 | 1.31 |
| 8.1956 | 6.8243 | 1.37 |
| 8.2414 | 7.0655 | 1.18 |
| 8.436 | 6.8576 | 1.29 |
| 8.6310 | 6.9645 | 1.67 |

Example 10

A wipe made in an identical manner to those in example 9 was prepared. On a plastic disposal cutting board (30 cm×30 cm) was applied one garlic clove freshly sliced into to two halves. The board was evenly rubbed by the garlic cloves to coat the surface of the board. The board surface smelled strongly of garlic odor as did the hand of the user. The board surface was wiped with a wipe along with the user hand. The board and user hand were then immediately assessed for garlic odor. There was no odor on the board or the user hands and no odor on the used wipe. Thus this example illustrates the novelty and utility of these pre-moistened wipes for odor control of surfaces both hard and soft.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged either in whole or in part. Furthermore, those of ordinary skill in the art will appreciate that the foregoing description is by way of example only, and is not intended to limit the invention so further described in such appended claims.

What is claimed:

1. A pre-moistened wipe comprising:
    a substrate: and
    a wiping solution contained in the substrate, the wiping solution comprising an odor control agent, the odor control agent comprising inorganic oxide particles modified with a transition metal, a quinone compound, or activated carbon particles, the wiping solution containing at least one surfactant, the at least one surfactant comprising a nonionic surfactant or an anionic surfactant, the wiping solution being substantially free of cationic surfactants, the wiping solution further comprising a carrier comprising water or an alcohol, the odor control agent being present in the substrate in an amount of at least about 80 mg or of at least about 2% by weight based on the dry weight of the substrate,
    wherein the transition metal forms an ionic bond with the inorganic oxide particles or the transition metal forms a coordinate or covalent bond with the inorganic oxide particles and wherein the substrate is configured to release from about 0.5 gsm to about 5 gsm of the odor control agent when contacted with an adjacent surface.

2. A pre-moistened wipe as defined in claim 1, wherein the odor control agent comprises the inorganic oxide particles modified with the transition metal, the inorganic oxide particles comprising silica particles, alumina particles, or mixtures thereof.

3. A pre-moistened wipe as defined in claim 1, wherein the odor control agent comprises the inorganic oxide particles modified with the transition metal, the inorganic oxide particles comprising silica particles, alumina particles, or mixtures thereof, the transition metal comprising salts of copper, iron, Manganese, cobalt, nickel, zinc, or mixtures thereof.

4. A pre-moistened wipe as defined in claim 3, wherein the inorganic oxide particles modified with the transition metal have a transition metal to inorganic oxide particle ratio of from about 25:1 to about 75:1 and have a surface area of less than about 200 m$^2$/g.

5. A pre-moistened wipe as defined in claim 3, wherein the transition metal comprises copper.

6. A pre-moistened wipe as defined in claim 3, wherein the transition metal comprises iron.

7. A pre-moistened wipe as defined in claim 3, wherein the transition metal comprises manganese.

8. A pre-moistened wipe as defined in claim 3, wherein the transition metal comprises cobalt.

9. A pre-moistened wipe as defined in claim 1, wherein the odor control agent comprises the quinone compound.

10. A pre-moistened wipe as defined in claim 1, wherein the odor control agent is present in the substrate in an amount from about 2% to about 30% by weight based on the dry weight of the substrate.

11. A pre-moistened wipe as defined in claim 1, wherein the at least one surfactant comprises a polyoxyethylene sorbitan monolaurate, a nonionic glycerin, lauric acid, castor oil, myristic acid, oleic acid, stearyl alcohol, cetyl alcohol, potassium laureth phosphate, capric acid, stearic acid, erucic acid, or mixtures thereof.

12. A pre-moistened wipe as defined in claim 1, wherein the wiping solution contains at least one nonionic surfactant and at least one anionic surfactant.

13. A pre-moistened wipe as defined in claim 1, wherein the wiping solution is contained in the substrate in an amount from about 150% to about 600% based on the dry weight of the substrate.

14. A pre-moistened wipe as defined in claim 1, wherein the wiping solution further comprises a sequestrant, a skin agent, and an antioxidant.

15. A pre-moistened wipe as defined in claim 1, wherein the substrate comprises a coform web, a wetlaid web, an airlaid web, or a hydroentangled web.

16. A pre-moistened wipe as defined in claim 1, wherein the wiping solution further comprises a fragrance, the fragrance comprising a non-hetero atom containing fragrance.

17. A pre-moistened wipe as defined in claim 1, wherein the fragrance comprises a terpene.

18. A pre-moistened wipe as defined in claim 1, wherein the transition metal forms an ionic bond with the inorganic oxide particles.

19. A pre-moistened wipe as defined in claim 1, wherein the transition metal forms a coordinate or covalent bond with the inorganic oxide particles.

* * * * *